US007491307B2

(12) United States Patent
Hsieh et al.

(10) Patent No.: US 7,491,307 B2
(45) Date of Patent: Feb. 17, 2009

(54) PORTABLE BIOAGENT CONCENTRATOR

(75) Inventors: H Ben Hsieh, Mountain View, CA (US); Meng H. Lean, Santa Clara, CA (US); Bryan T. Preas, Palo Alto, CA (US); Armin R. Volkel, Mountain View, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 934 days.

(21) Appl. No.: 10/838,937

(22) Filed: May 4, 2004

(65) Prior Publication Data

US 2005/0247565 A1 Nov. 10, 2005

(51) Int. Cl.
*G01N 27/453* (2006.01)

(52) U.S. Cl. .................. 204/643; 204/600

(58) Field of Classification Search ................ 204/450, 204/600, 547, 643

See application file for complete search history.

(56) References Cited

U.S. PATENT DOCUMENTS 4,289,270 A 9/1981 Warsinske ................ 233/27
4,301,118 A 11/1981 Eddleman et al. .......... 422/101
5,632,957 A 5/1997 Heller et al. .............. 422/68.1
5,653,859 A 8/1997 Parton et al. .............. 204/450
6,013,165 A * 1/2000 Wiktorowicz et al. ....... 204/456
6,272,296 B1 8/2001 Gartstein .................... 399/55
6,355,491 B1 3/2002 Zhou et al. ................. 436/518
6,751,832 B2 * 6/2004 Hirota et al. .............. 29/25.35
7,156,970 B2 1/2007 Lean et al.
7,163,611 B2 1/2007 Volkel et al.
7,282,129 B2 10/2007 Lean et al.
2004/0038249 A1 * 2/2004 Darteil et al. ................ 435/6

OTHER PUBLICATIONS

Dunphy et al. "Rapid Separation and Manipulation of DNA by a Ratcheting Electrophoresis Microchip (REM)," Proceedings of IMECE2002, Nov. 17-22, 2002, New Orleans, LA., No. IMECE2002-33564.

U.S. Appl. No. entitled "Continuous Flow Particle Concentrator" to Armin R. Volkel et al., filed May 4, 2004.

* cited by examiner

*Primary Examiner*—Alex Noguerola
(74) *Attorney, Agent, or Firm*—Fay Sharpe LLP

(57) ABSTRACT

A portable apparatus for extracting and concentrating bioagents within a fluid medium includes a container with sample solution inlet port and traveling wave grids patterned on surfaces of the container. The traveling wave grids cause bioagents to migrate to a specified surface within the container and then to an extraction port. The traveling wave grids include a substrate, across which extend a collection of closely spaced and parallel electrically conductive electrodes, and a collection of buses providing electrical communication with the collection of conductive electrodes. A voltage controller provides a multiphase electrical signal to the collection of buses and electrodes of the traveling wave grids.

19 Claims, 9 Drawing Sheets

PORTABLE BIOAGENT CONCENTRATOR

STATEMENT REGARDING FEDERALLY SPONSORED RESEARCH OR DEVELOPMENT

This invention was made with Government support under DAAD19-03-C-0116 awarded by U.S. Army. The Government has certain rights in this invention.

CROSS REFERENCE TO RELATED APPLICATIONS

The following copending applications, U.S. application Ser. No. 10/460,137, filed Jun. 12, 2003, titled "Traveling Wave Algorithms to Focus and Concentrate Proteins in Gel Electrophoresis", U.S. application Ser. No. 10/459,799, filed Jun. 12, 2003, titled "Distributed Multi-segmented Reconfigurable Traveling Wave Grids for Separation of Proteins in Gel Electrophoresis", U.S. application Ser. No. 10/727,289, filed Dec. 3, 2003, titled "Concentration and Focusing of Bio-agents and Micron-sized Particles Using Traveling Wave Grids", and U.S. application Ser. No. 10/838,570, filed May 4, 2004, titled "Continuous Flow Particle Concentrator", are assigned to the same assignee of the present application. The entire disclosures of these copending applications are totally incorporated herein by reference in their entirety.

INCORPORATION BY REFERENCE

The following U.S. patents are fully incorporated herein by reference: U.S. Pat. No. 4,289,270 to Warsinke ("Portable Concentrator"); U.S. Pat. No. 4,301,118 to Eddleman et al. ("Protein Concentrator"); U.S. Pat. No. 5,632,957 to Heller et al. ("Molecular Biological Diagnostic Systems Including Electrodes"); U.S. Pat. No. 6,272,296 to Gartstein ("Method and Apparatus Using Traveling Wave Potential Waveforms for Separation of Opposite Sign Charge Particles"); and U.S. Pat. No. 6,355,491 to Zhou et al. ("Individually Addressable Micro-electromagnetic Unit Array Chips").

BACKGROUND

This disclosure relates generally to the field of electrophoretic separation of bio-agents and particles, and more particularly, to systems and devices for focusing the bio-agents into regions of relatively high concentrations.

Electrophoresis is a separation technique most often applied to the analysis of biological or other polymeric samples. It has frequent application to analysis of proteins and DNA fragment mixtures. The high resolution of electrophoresis has made it a key tool in the advancement of biotechnology. Variations of this methodology are used for DNA sequencing, isolating active biological factors associated with diseases such as cystic fibrosis, sickle-cell anemia, myelomas, and leukemia, and establishing immunological reactions between samples on the basis of individual compounds. Electrophoresis is an extremely effective analytical tool because it does not affect a molecule's structure, and it is highly sensitive to small differences in molecular charge and mass.

Particles can be manipulated by subjecting them to traveling electric fields. Such traveling fields are produced by applying appropriate voltages to microelectrode arrays of suitable design. Traveling electric fields are generated by applying voltages of suitable frequency and phases to the electrodes.

This technique of using traveling electric fields relates to an important method for separation and sorting of large particles and cells referred to as dielectrophoresis. Dielectrophoresis is defined as the movement of a polarizable particle in a non-uniform electric field. Essentially, the force arises from the interaction of the field non-uniformity with a field-induced charge redistribution in the separated particle.

Particles are manipulated using non uniform electric fields generated by various configurations of electrodes and electrode arrays. As a general biotechnological tool, dielectrophoresis is extremely powerful. From a measurement of the rate of movement of a particle the dielectric properties of the particle can be determined. More significantly, particles can be manipulated and positioned at will without physical contact, leading to new methods for separation technology.

A powerful extension of dielectrophoresis separation is traveling wave dielectrophoresis (TWD) in which variable electric fields are generated in a system of electrodes by applying time varying electric potential to consecutive electrodes. Such a method of Traveling Wave Field Migration was described by Parton et al. in U.S. Pat. No. 5,653,859, herein incorporated by reference. Although satisfactory, a need for improved strategies and methodologies remains. In addition, dielectrophoresis requires higher voltage (~100 V), higher frequencies (~10 MHZ), and finer electrode pitch (<10 um).

A microfluidic device for electrophoretic separation of biomolecules such as DNA and protein was described by Dunphy et al. in "Rapid Separation and Manipulation of DNA by a Ratcheting Electrophoresis Microchip (REM)," Proceedings of IMECE2002, Nov. 17-22, 2002, New Orleans, La., No. IMECE2002-33564, herein incorporated by reference. The device utilizes thousands of electrodes along the length of a microchannel. An electrical potential is applied across the electrodes and selectively varied to separate molecules within the microchannel into two groups using a ratcheting mechanism. This mechanism does not employ traveling waves. Although directed to the separation of biomolecules, this strategy is based upon micro device technology and is not readily compatible with conventional laboratory equipment. Accordingly, a need exists for a device and technique for utilizing electrostatic traveling waves for selectively concentrating bio-agents and particles, and particularly, for subsequent analysis.

Detection of miniscule amounts of bio-agents, such as toxins, viruses, spores, etc., is important in the bio-sciences, particularly with respect to public health matters and the protection of emergency and military personnel. However, these bioagents are often life-threatening at miniscule concentrators and undetectable without concentration. Laboratory procedures may provide up to two orders of magnitude of concentration (e.g. ultra filtration) for biomolecules, but filtration is a lengthy process and requires a high-pressure source not readily available in the field. Therefore, there is a need for a compact, portable device to extract charged bio-agents (e.g. toxins, viruses, weaponized bacteria or their spores, or oocytes of harmful parasites, etc.) that are suspended in a liquid, concentrate them in a high viscosity medium and focus them into a detector.

BRIEF SUMMARY

The disclosed embodiments provide examples of improved solutions to the problems noted in the above Background discussion and the art cited therein. There is shown in these examples an improved portable apparatus for extracting and concentrating bioagents within a fluid medium. The apparatus includes a container with sample solution inlet port and traveling wave grids patterned on surfaces of the container. The traveling wave grids cause bioagents to migrate to a specified surface within the container and then to an extraction port. The traveling wave grids include a substrate, across which extend a collection of closely spaced and parallel electrically conductive electrodes, and a collection of buses providing electrical communication with the collection of conductive electrodes. A voltage controller provides a multiphase electrical signal to the collection of buses and electrodes of the traveling wave grids.

BRIEF DESCRIPTION OF THE DRAWINGS

The foregoing and other features of the embodiments described herein will be apparent and easily understood from a further reading of the specification, claims and by reference to the accompanying drawings in which:

DETAILED DESCRIPTION

The portable particle concentrator uses electrostatic fields and traveling wave grids to concentrate charged biomolecules, such as spores, viruses, toxins, etc., in the liquid phase. The portable particle concentrator includes an inlet for a sample solution introduction, a set of electrical grids on the inner sides and bottom of the device, a port for concentrated sample retrieval, and an interface with portable power sources and controller for extended operation. In the liquid phase, with water as the medium, the majority of biomolecules carry charges. By biasing the voltage on the two sides, charged biomolecules are directed toward the two walls and concentrated. Two-dimensional traveling waves on the walls are concurrently swept across both surfaces and the bottom plate to focus these charged particles to single points, where they may be retrieved with a syringe. Focusing occurs simultaneously with operation of the biased field until the molecules on the surfaces are moved to the retrieval port. A charge control agent may be added to the sample solution to alter the pH to provide charge to those biomolecules having isoelectric points at the pH of the sample that would otherwise be neutral. The portable concentrator may be utilized as an additional process step for water already concentrated by another process, such as tangential flow filtration, to further concentrate and reduce the sample size.

Figure 1:
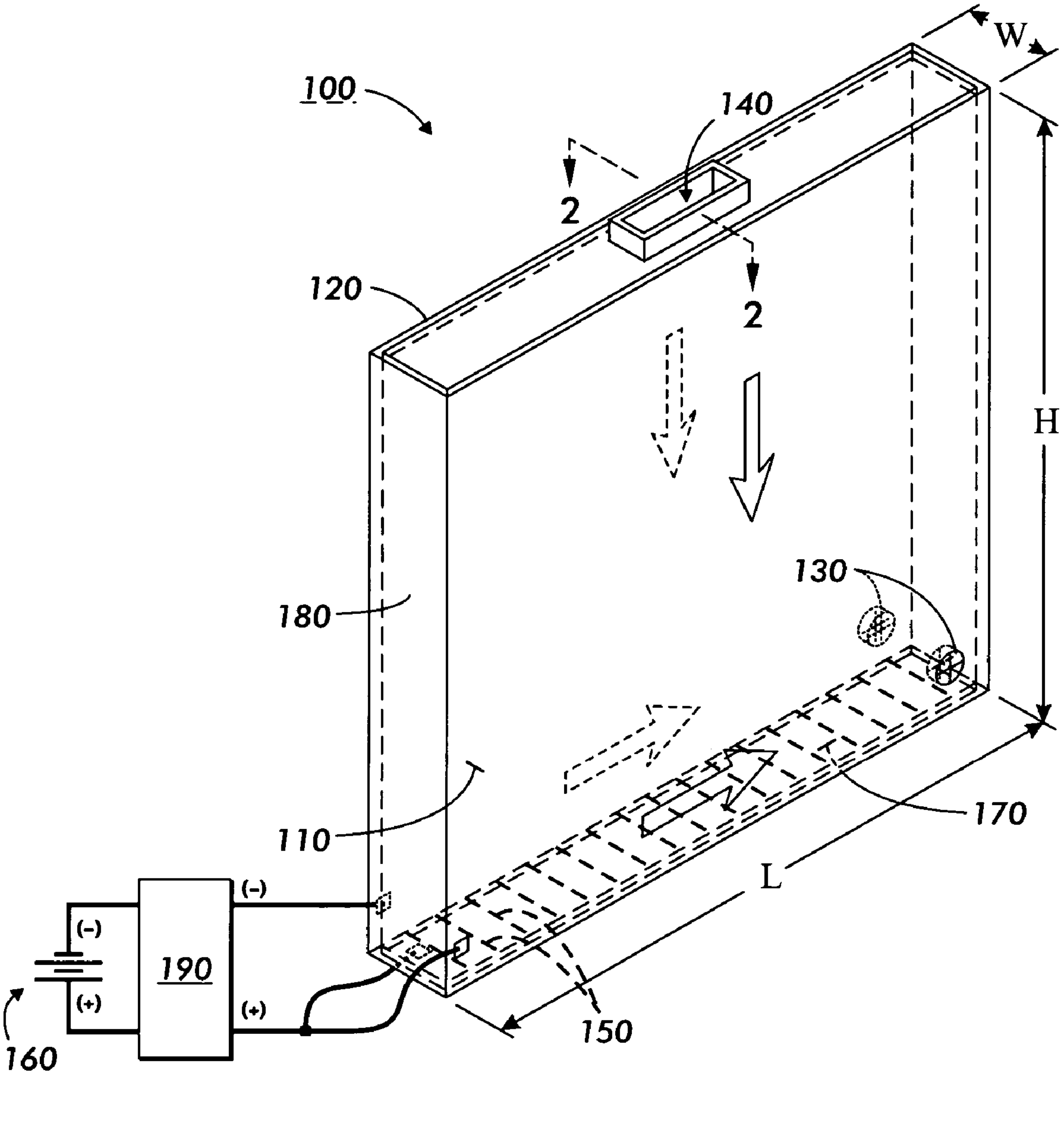
FIG. 1 is a perspective illustration of one embodiment of the portable particle concentrator.

FIG. 1 shows a perspective view of an example embodiment of the portable particle concentrator. This embodiment is in the form of a parallelepiped having sides 110 and 120, which have a height H and a length L. For the purposes of describing an approximately liter-sized concentrator which would be hand portable, the sides may be twenty centimeters in both height and length. An input port 140, located on a top plate 170, permits sample introduction and outlet ports 130 for concentrated sample retrieval are provided at the lower corners of each of sides 110 and 120. While for the purposes of this discussion input port 140 is located in the center of the top plate, it will be appreciated that it may be placed at any location on the top plate or at the top corner of either of the end plates 180. Additionally, the inlet port may take any form convenient for the introduction and decanting of processed water, such as a circular configuration. The inlet port cover mechanism may take any of many forms known in the art.

Two dimensional traveling wave grids 150 are patterned on the inside of side plates 110 and 120 and on bottom plate 170. For the purposes of the description of this embodiment, the traveling wave grids may have a grid width of 10 μm and a pitch of 40 μm, although those skilled in the art will appreciate that other configurations would be possible, all of which are contemplated by the scope of the specification and claims herein. The pitch may be optimized to a particular particle size range and effective fringing field height. The traveling wave grid includes a substrate, a collection of closely spaced and parallel electrically conductive electrodes extending across the substrate, and a collection of buses providing electrical communication with the collection of electrodes. The surface of the traveling wave grid may include a thin (for example 20 μm) coating of polymer or gel to entrain the bioagents and mitigate back diffusion. The traveling wave grids may be fabricated on 4-inch wafers, with four such wafers tiled for each collection side.

The portable particle concentrator also includes connection for a controller 190 and for portable battery 160. After a water sample is introduced through sample inlet 140, the inlet is closed and traveling waves and bias voltages are applied to the two side plates 110 and 120, with up to +/−50V relative to the ground on each side. Biomolecules with isoelectric points (pI) higher than the pH of the sample solution carry positive charges and experience the pull from the negative plate located on side 120. Similarly, biomolecules with lower pI have negative charges and are pulled toward the positive plate located on side 110. While these charged particles are pulled to the side plates of the device, traveling waves are applied simultaneously to move these molecules in direction $d_1$ toward bottom plate 180, where another traveling wave grid 150 moves the molecules in direction $d_2$ toward the corners of the device. Concurrent operation of the traveling wave grids reduces bioagent accumulation on the grids while focusing them onto retrieval ports 130. Operation of the traveling wave grids is further described in U.S. patent application Ser. No. 10/727,289, "Concentration and Focusing of Bio-agents and Micron-sized Particles Using Traveling Wave Grids", incorporated by reference hereinabove.

Figure 2:
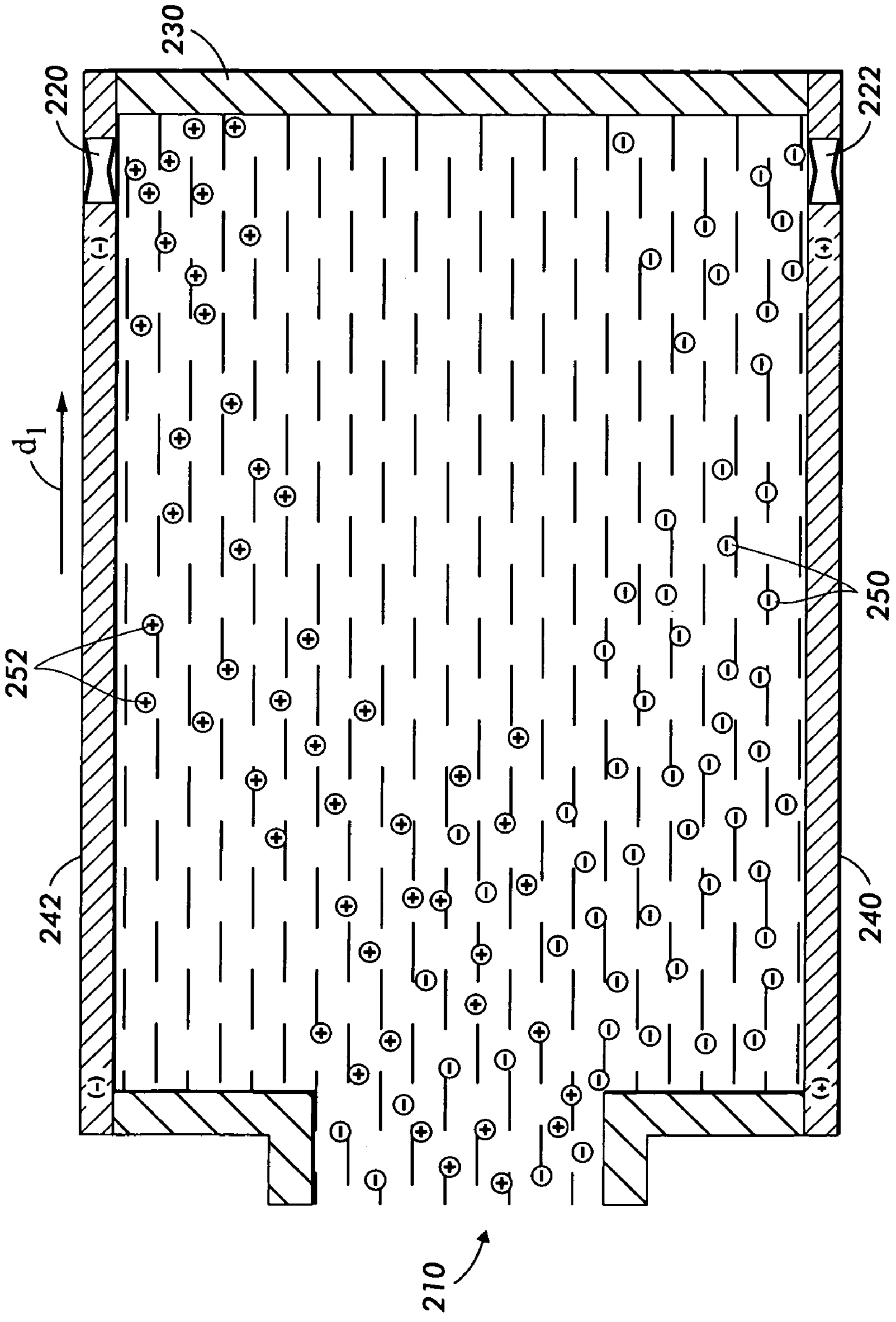
FIG. 2 is a schematic illustration of the portable particle concentrator according to the embodiment of FIG. 1.

Turning now to FIG. 2, there is shown a schematic cross-sectional view of one example embodiment of the particle concentrator. In this embodiment, liquid sample is introduced at inlet port 210. Two dimensional traveling wave grids are patterned on the inside of side plates 240 and 242 and on bottom plate 230. For the purposes of the description of this embodiment, the traveling wave grids may have a grid width of 10 μm and a pitch of 40 μm, although those skilled in the art will appreciate that other configurations would be possible, all of which are contemplated by the scope of the specification and claims herein. For example, a 100 um pitch with 50 um electrode width and 200 um pitch with 100 um electrode width both work well for particle sizes up to 20 um. Optimal dimension selection may be made through simulation. The traveling wave grid includes a substrate, a collection of closely spaced and parallel electrically conductive electrodes extending across the substrate, and a collection of buses providing electrical communication with the collection of electrodes. The surface of the traveling wave grid may include a thin (for example 20 μm) coating of polymer or gel to entrain the bioagents and mitigate back diffusion. The traveling wave grids may be fabricated on 4-inch wafers, with four such wafers tiled for each collection side.

The portable particle concentrator also includes connections (not shown) for portable battery power. After a water sample is introduced through sample inlet 210, the inlet is closed and power is supplied to the two side plates 240 and 242, with up to +/−50V relative to the ground on each side. Biomolecules 252 with isoelectric points (pI) higher than the pH of the sample solution carry positive charges and experience the pull from the negative plate located on side 242. Similarly, biomolecules 250 with lower pI have negative charges and are pulled toward the positive plate located on side 240. While these charged particles are pulled to the side plates of the device, traveling waves are applied simultaneously to move these molecules in direction d, toward bottom plate 230, where another traveling wave grid moves the molecules toward the collection ports 220 and 222 of the device. Concurrent operation of the traveling wave grids reduces bioagent accumulation on the grids while focusing them onto retrieval ports 220 and 222.

Figure 3:
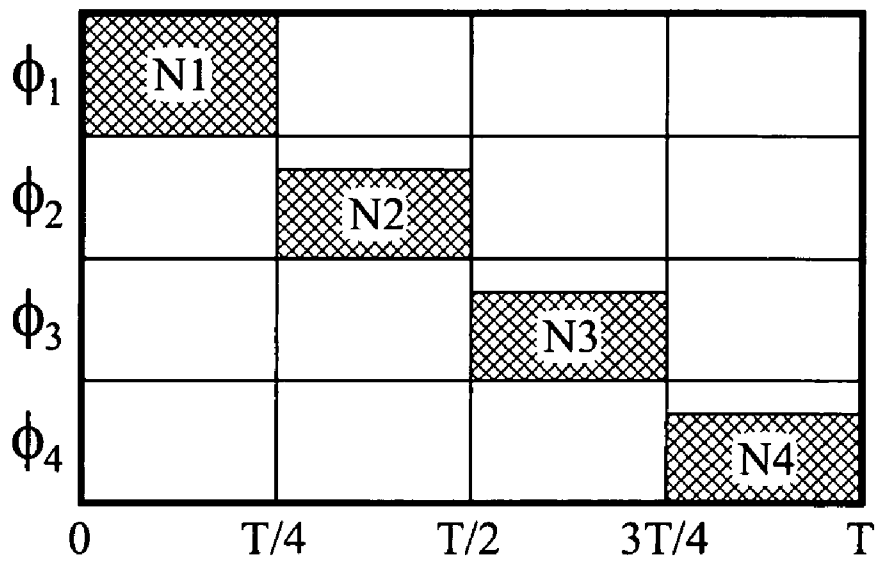
FIG. 3 is a representative four phase traveling wave voltage pattern employed in the traveling wave grids.

FIG. 3 is a representative four phase voltage pattern or waveform used in the example embodiment systems and traveling wave grids of the particle concentrator. For the purposes herein, the four phase voltage waveform has a 90 degree separation between phases. Each waveform occurring in each phase is a square wave pulse, with each pulse sequentially applied to an adjacent electrode. Thus, a first pulse in phase N1 is applied to a first electrode for a desired time period, such as T/4. Upon completion of that first pulse, such as at time T/4, a second pulse in phase N2 is applied to a second electrode, which may be immediately adjacent to the first electrode. Upon completion of that second pulse, such as at time T/2, a third pulse in phase N3 is applied to a third electrode, which may be adjacent to the second electrode. Upon completion of that third pulse, such as at time 3T/4, a fourth pulse in phase N4 is applied to a fourth electrode, which may be adjacent to the third electrode. This sequential and ordered array of voltage pulsing results in bio-agents or particles dispersed in the liquid to "hop" from the vicinity of one electrode to another.

Figure 4:
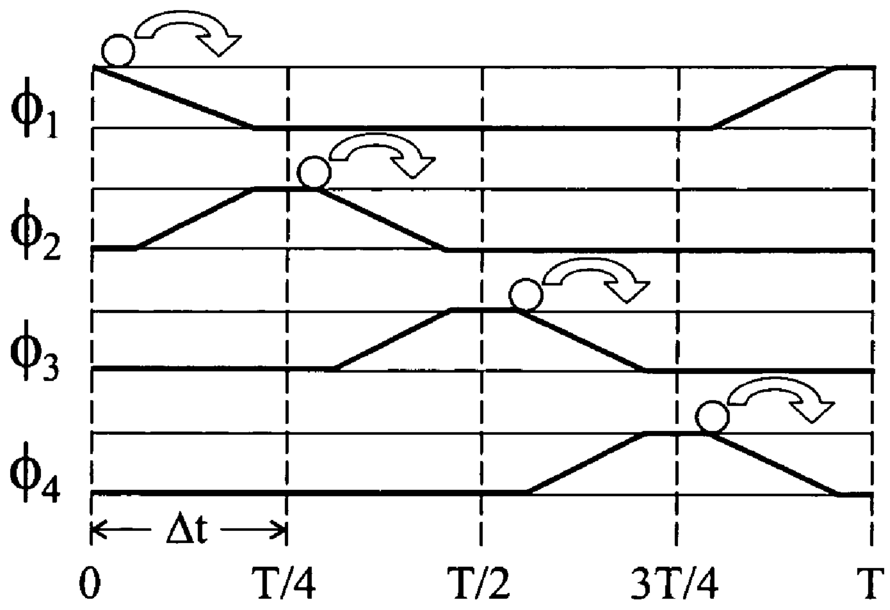
FIG. 4 is a schematic illustration of biomolecule transport from one electrode to another.

The synchronous mode of propagation is depicted in FIG. 4 and may be described as a "hopping" mode where the bio-agent or particles hop from electrode to electrode in the direction of the pulse train. The transit time to migrate across the dielectric space is then given by:

$$t_{transit}=s/\mu E,$$

where pitch is given by p=w+s, and w and s are the electrode width and dielectric space, respectively. Electric field and mobility are given by E and μ, respectively. The period for one cycle through the four phases is $4*t_{transit}$, so that the maximum sweep frequency is:

$$f<\mu E/4s.$$

For sustained transport, the bio-agent or particle has to have sufficient speed (μE) and time ($t_{transit}$) to traverse the distance of the dielectric space, s. This equation implies that for sustained transport, there is a critical frequency for bio-agents or particles of a certain mobility. Therefore, by starting with the highest operational frequency, one can progressively scan downwards in frequency until the bio-agent or particle of the right mobility starts to move. This means that for certain bio-agents, the fastest (and lowest molecular weight) bio-agents, i.e. biomolecules, may be separated out from the sample one at a time.

Figure 5:
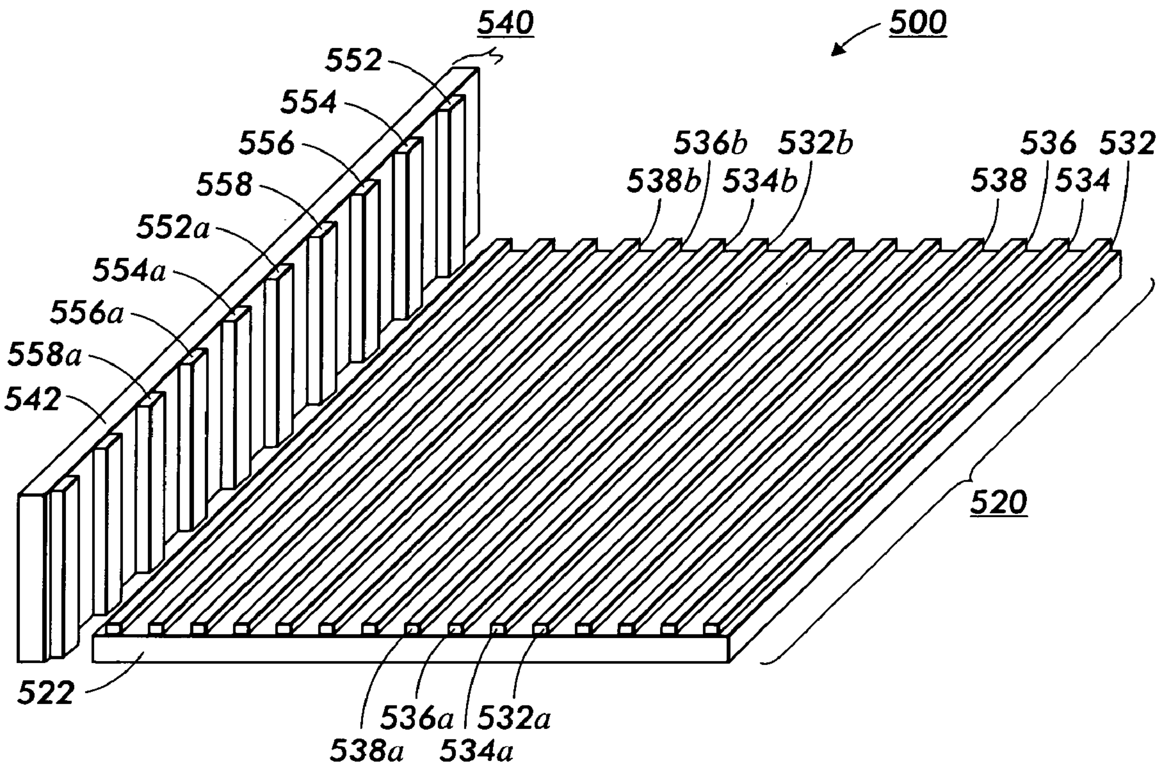
FIG. 5 is a schematic illustration of an example configuration of traveling wave grids.

Referring to FIG. 5, a traveling wave grid system 500 is illustrated. The system 500 comprises a first traveling wave grid 520 including a substrate 522 and a plurality of electrodes 532, 534, 536, and 538; 532*a*, 534*a*, 536*a*, and 538*a*; and 532*b*, 534*b*, 536*b*, and 538*b*. The system 500 also comprises a second traveling wave grid 540 including a substrate 542 and a plurality of electrodes 552, 554, 556, and 558; and 552*a*, 554*a*, 556*a*, and 558*a*. The grids 520 and 540 are arranged at angles with respect to each other, within the ranges of 10° to 170°, 80° to 100°, or at 90°. In this configuration all charged particles that are within the reach of the electric field generated from grid 520 are moved to the wall of grid 540. That is, particles suspended above the grid 520 are transported toward the grid 540, which in FIG. 5, is towards the left side of the grid 520. The grid 540 moves the particles along the corner or region of intersection of the grids 540 and 520, and concentrates the particles either in one region that is determined by the pulse sequence of the waveform or at one of the ends of grid 540, such as where a detector is placed. If diffusion of the particles is sufficiently suppressed (e.g. by using a high-viscosity transport medium), the particles will remain confined in a small area near the corner of the grids, and the second grid 540 can concentrate them into a single small region, i.e. typically less than 1 $cm^3$ or 1 mL.

Referring further to FIG. 5, in one embodiment, grid 520 concentrates the particles in line(s) parallel to its electrodes. The extent and manner of concentration depends on the pulse sequence and transport medium properties. Grid 540 concentrates the particles further into one or more individual regions of relatively high particle concentration. Because the effectiveness of a traveling wave grid decreases the further the particles are located from its electrodes, a biasing grid can provide a bias voltage to keep the particles in a thin layer just above the active grid and can also maintain a bias voltage to keep the particles from escaping from this layer while they are undergoing transport.

Figure 6:
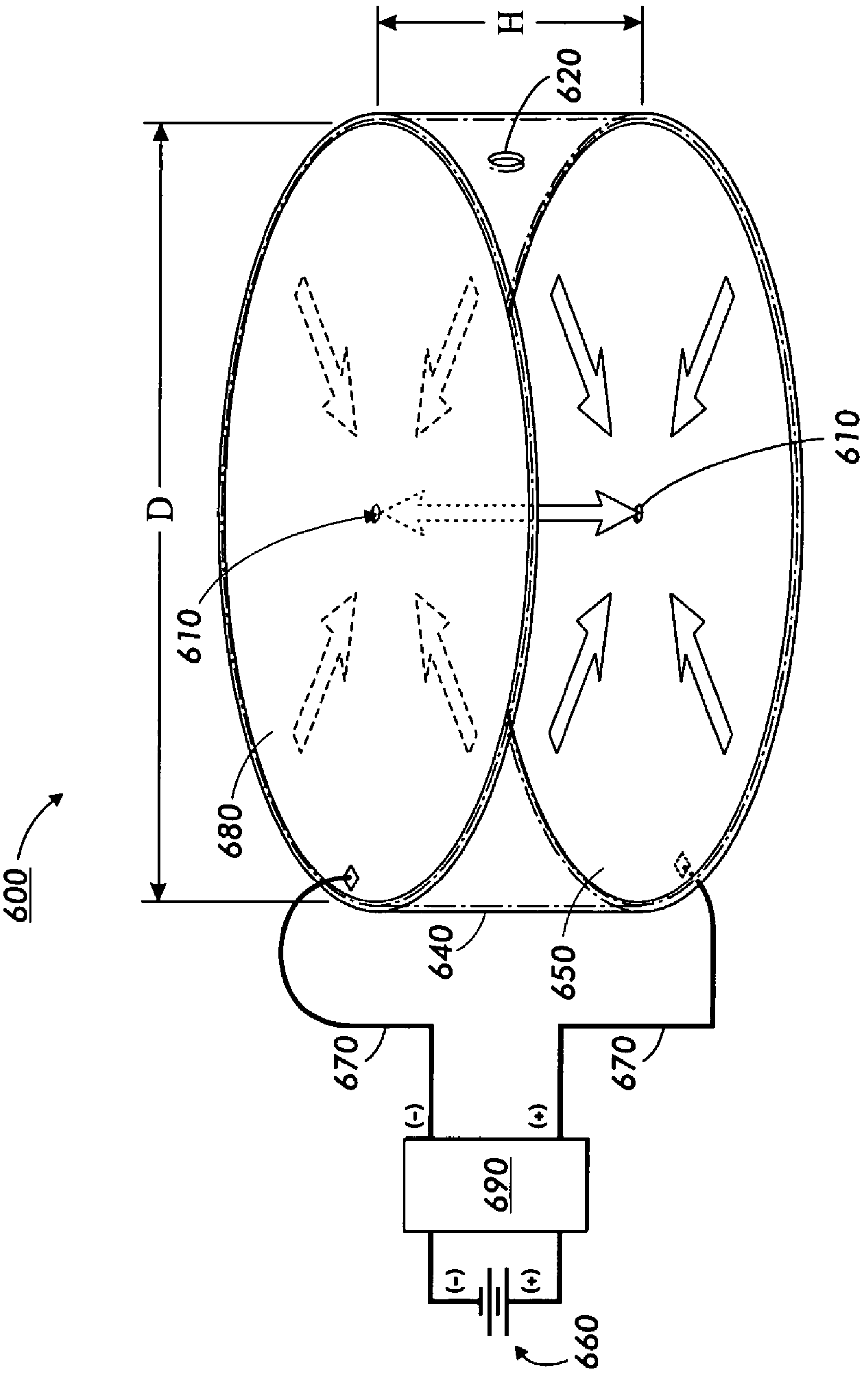
FIG. 6 is a perspective illustration of another embodiment of the portable particle concentrator.
Figure 7:
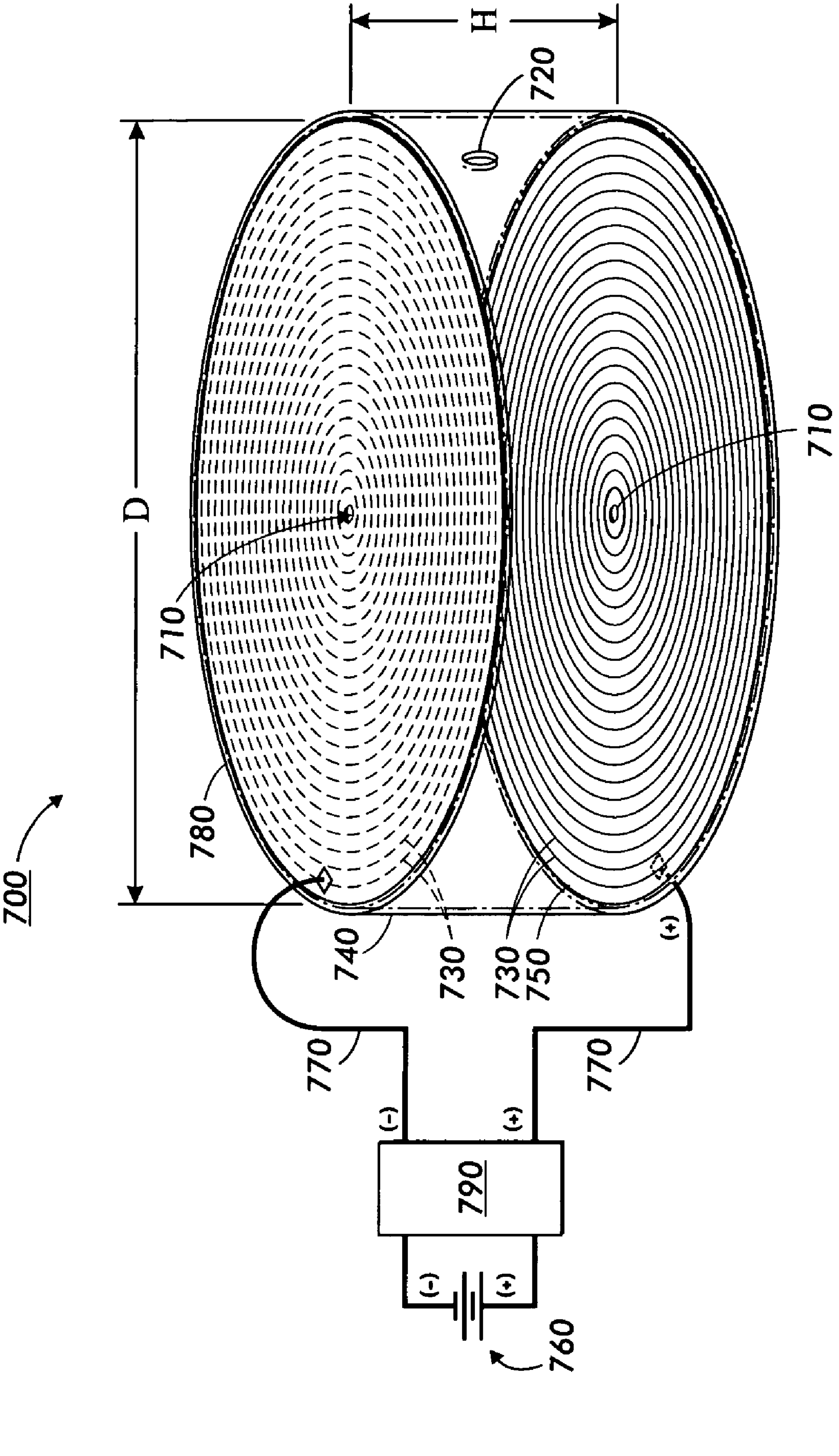
FIG. 7 is a schematic illustration of the portable particle concentrator according to the embodiment of FIG. 6.

Turning now to FIGS. 6 and 7, a perspective diagram of another embodiment of the portable particle concentrator is illustrated. This embodiment is in the form of a cylinder having side 640 with a height H and top and bottom plates 680 and 650, respectively, both having a diameter D. For an approximately liter-sized concentrator, the sides may be approximately 2.2 inches in height with the diameter of top and bottom plates 680 and 650 being approximately 6 inches. Alternatively, a 2 inch diameter and 1 inch height would provide a total volume of approximately 50 mL, and other height and length specifications could also be utilized, as will be appreciated by one skilled in the art. Inlet port 620, located on side wall 640 permit sample introduction. Retrieval ports 610, located in both top and bottom plates 680 and 650, provide for concentrated sample retrieval from either side of the device. Covering or latching mechanisms for inlet port 620 and sample retrieval ports 610 may utilize any of numerous forms known in the art, such as flaps, an iris structure, etc.

Two dimensional traveling wave grids 630 are patterned on the inside of plates 680 and 650 and can be seen in FIG. 7 as grids 730. For the purposes of the description of this embodiment, the traveling wave grids may have a grid pitch of 40 μm, although those skilled in the art will appreciate that other configurations would be possible, all of which are contemplated by the scope of the specification and claims herein. Each of the traveling wave grids includes a substrate, a collection of closely spaced and concentric electrically conductive electrodes extending across the substrate, and a collection of buses providing electrical communication with the collection of electrodes. The surface of the traveling wave grids may include a thin (for example 20 μm) coating of polymer or gel to entrain the bioagents and mitigate back diffusion. The traveling wave grids may be fabricated on wafers of varying dimensions.

The portable particle concentrator also includes connection 670 for portable battery pack 660 and controller 690. After a water sample is introduced through a selected sample inlet 620, a biased electric field is applied to force charged biomolecules toward the opposing plate, to which power is supplied. For example, when a sample is introduced through inlet port 620 in side wall 640, then the electric field causes the charged biomolecules to migrate toward bottom plate 650, to which power is supplied, with up to +/−50V relative to the ground. Traveling waves are applied to concentrate these molecules toward the center and sample retrieval port 610 in bottom plate 650. The bias and traveling wave voltages are applied by the controller 690. As a result the traveling wave voltages are superimposed on top of the bias voltages. Alternatively, the biased field direction may be inverted to concentrate particles of opposite charges.

In another embodiment, top and bottom plates 680 and 650 are oppositely charged, to enable the separation and retrieval of oppositely-charged particles. In this embodiment, biomolecules with isoelectric points (pI) higher than the pH of the sample solution carry positive charges and experience the pull from the negative plate 680. Similarly, biomolecules with lower pI have negative charges and are pulled toward the positive plate 650. While these charged particles are pulled to the top or bottom plates of the device, traveling waves are applied simultaneously to move these molecules toward the center of each plate. Operation of the traveling wave grids is further described in U.S. patent application Ser. No. 10/727,289, "Concentration and Focusing of Bio-agents and Micron-sized Particles Using Traveling Wave Grids", incorporated by reference hereinabove.

Figure 8:
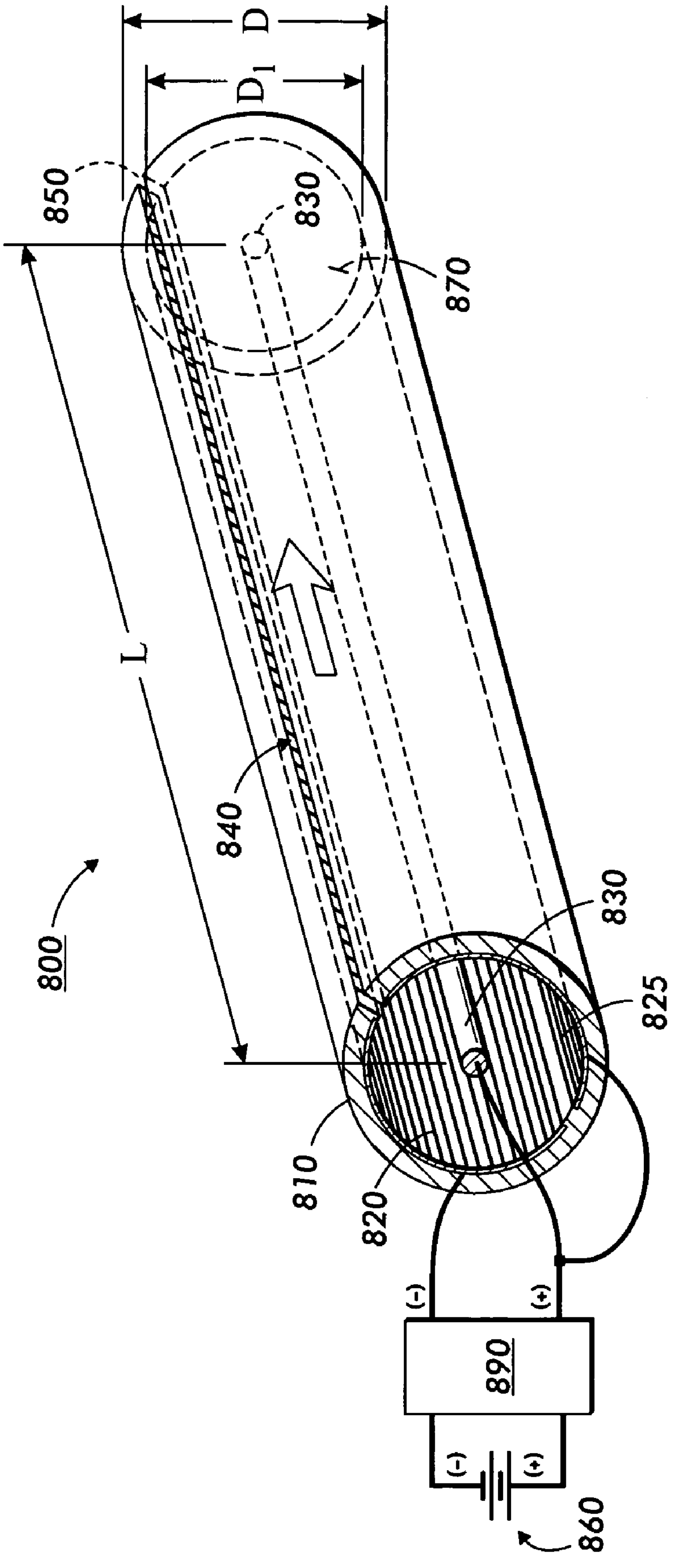
FIG. 8 is a perspective illustration of yet another embodiment of the portable particle concentrator.

Referring now to FIG. 8, a schematic diagram of another embodiment of the portable particle concentrator is illustrated. In this embodiment, traveling wave grids 820 and 825 are located in the inner surface of cylinder wall 810 and run parallel to the length L of the device up to collection slot 850. Collection slot 850 includes traveling wave grid 840, which runs perpendicular to the length of the particle concentrator. Side plates 870 have a diameter D, that can be closed after the container is filled. The inner cylindrical (fluid) core will have a diameter of $D_1$ and includes a center electrode 830. The traveling waves and bias voltages are produced by a controller 890.

Figure 9:
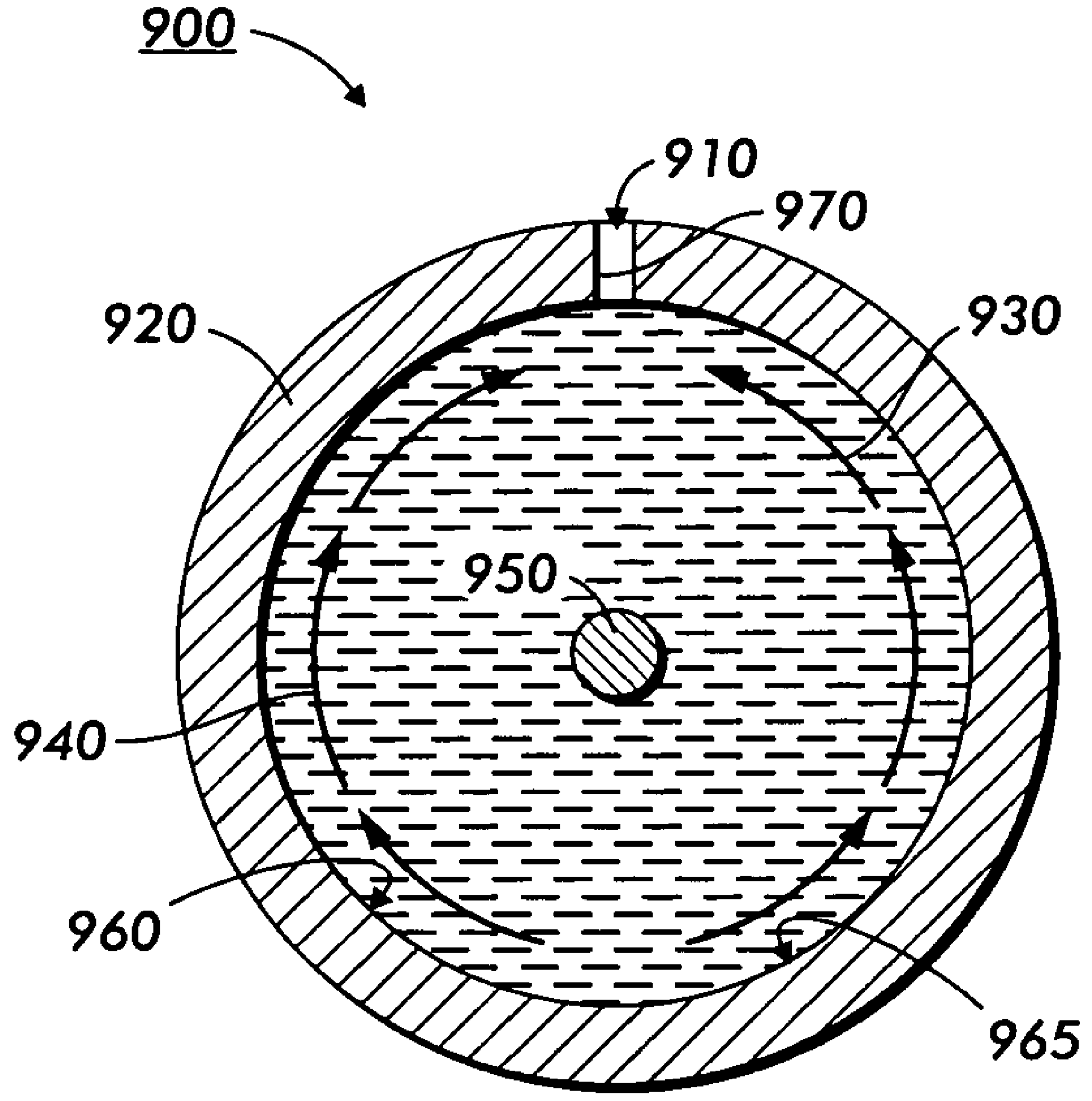
FIG. 9 is a schematic illustration of the portable particle concentrator according to the embodiment of FIG. 8.

As can be seen in FIG. 9, traveling wave grids 965 will transport molecules counterclockwise in direction 930 to the collection trench and traveling wave grids 960 have an opposite direction and will transport molecules clockwise in direction 940 until both meet at the collection trench 910. Traveling wave grid 970 in the collection trench will further transport molecules along the length of the device toward the back wall. For a portable concentrator, the cylindrical core $D_1$ diameter may be approximately 2 inches and the length of the concentrator can be 6 inches, which will yield a fluid volume of approximately 300 mL when filled. In one embodiment, this device may be operated after the fluid core is filled and the side plates are closed. In this mode, the center electrode will have a biased voltage relative to the traveling wave grids on the inner surface of the shell so that oppositely charged molecules will be attracted to the traveling wave grids. Simultaneously, a traveling wave is applied so that molecules will be swept toward the collection trench. At the collection trench, molecules will experience a traveling wave electric field perpendicular to the length of the device so they are further transported to the collection slit at the end plate where they can be retrieved (e.g. with a syringe). However, if higher process volume is desired, the device can be connected to a larger reservoir and slowly the sample water can be flowed through the cylinder core. In such an embodiment, an opening on the top plate will allow proper tubing to be connected and a small peristaltic pump can be used to pump sample water from reservoir to the device. There will be a similarly-sized opening in the bottom plate with properly connected tubing that can drain the processed water out. Flow rate can be adjusted through the pump depending on the process time and volume of the sample water.

Figure 10:
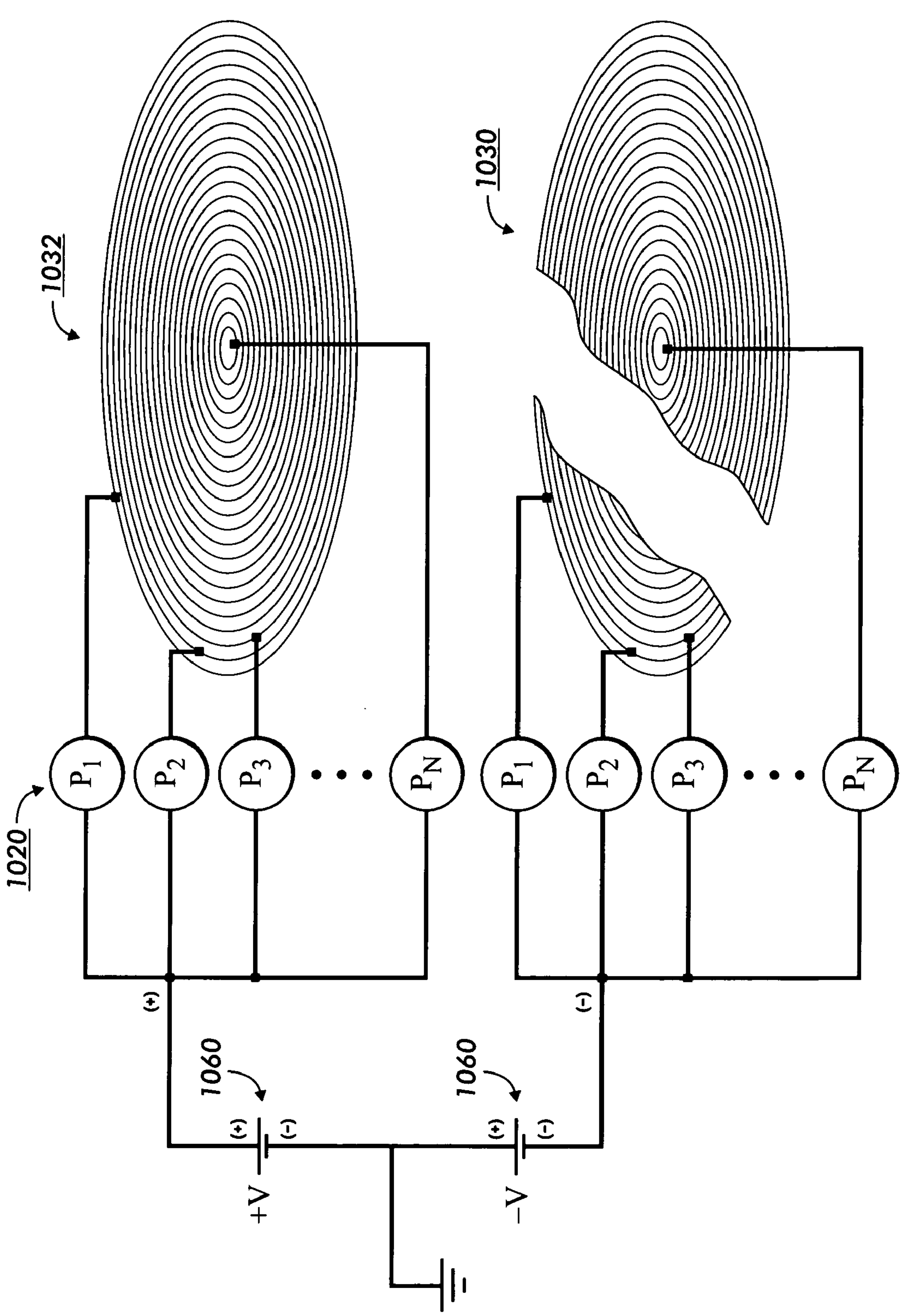
FIG. 10 is an electrical diagram illustrating the operation of one embodiment of a controller that produces traveling wave bias voltages.

Turning now to FIG. 10 an electrical diagram illustrates the operation of one embodiment of a controller that produces traveling wave bias voltages. The controller uses the power of battery to produce positive and negative bias voltages 1060 and to produce the traveling wave pulses 1020 on traveling wave grids 1030 and 1032. For the purposes of clarity, only four positive pulses provided to four electrodes on a first traveling wave grid 1032 and four negative pulses provided to another traveling wave grid 1030 are shown. However, it will be appreciated that a traveling wave grid may have numerous electrodes, with each electrode being driven by a separate traveling wave pulse. The traveling wave pulses may be applied sequentially or simultaneously, depending on the configuration of the portable particle concentrator and the desired concentration results.

While the present discussion has been illustrated and described with reference to specific embodiments, further modification and improvements will occur to those skilled in the art. For example, any of the embodiments described herein could be utilized to operate the traveling wave grid as a high pass filter to collect only those particles with mobilities above a threshold value. Additionally, the bio-agents to be collected may be pre-selected through customization of traveling wave grid parameters, such as pulse sequence or frequency. It is to be understood, therefore, that this disclosure is not limited to the particular forms illustrated and that it is intended in the appended claims to embrace all alternatives, modifications, and variations which do not depart from the spirit and scope of the embodiments described herein.

What is claimed:

1. A portable apparatus for extracting and concentrating bioagents within a fluid medium, the apparatus comprising:

a container having at least one sample solution inlet port;

at least two traveling wave grids patterned on at least two surfaces of said container, wherein at least one traveling wave grid causes bioagents to migrate to at least one specified surface within said container to at least one extraction port, said at least two traveling wave grids comprising:

a substrate;

a collection of closely spaced and parallel electrically conductive electrodes extending across said substrate; and a collection of buses providing electrical communication with said collection of conductive electrodes; and at least one voltage controller for providing a multiphase electrical signal to said collection of buses and said collection of electrodes of said at least two traveling wave grids.

2. The portable apparatus for extracting and concentrating bioagents according to claim 1, wherein said collection of electrodes is driven in a four phase voltage waveform having a ninety degree separation between said phases.

3. The portable apparatus for extracting and concentrating bioagents according to claim 2, wherein said waveform is a square wave pulse wherein each pulse is sequentially applied to an adjacent electrode in said collection of electrodes.

4. The portable apparatus according to claim 3, wherein the apparatus has a means for generating a pulse sequence or frequency that is customized to preselect specified types of bioagents.

5. The portable apparatus for extracting and concentrating bioagents according to claim 1, wherein a first traveling wave grid is configured in an arrangement to cause the bioagents to migrate to at least one specified surface within said container and a second at least one traveling wave grid is configured in an arrangement to cause the bioagents to migrate from said at least one specified surface to at least one extraction port.

6. The portable apparatus according to claim 1, wherein said at least two traveling wave grids comprise three traveling wave grids patterned on three surfaces of said container, wherein a first traveling wave grid and a second traveling wave grid are patterned on opposing surfaces of said container and a third traveling wave grid is patterned on a surface adjacent to both said first traveling wave grid and said second traveling wave grid.

7. The portable apparatus according to claim 6, wherein said first traveling wave grid and said second traveling wave grid is configured in an arrangement to cause the bioagents to migrate to at least one specified surface within said container and said third traveling wave grid is configured in an arrangement to cause said bioagents to migrate from said at least one specified surface to at least one extraction port.

8. The portable apparatus according to claim 7, wherein said first traveling wave grid is oppositely charged from said second traveling wave grid.

9. The portable apparatus according to claim 1, wherein said at least two traveling wave grids are patterned on opposing end plates of a cylinder, and wherein at least one of said two circular traveling wave grids causes bioagents to migrate to at least one extraction port located at the center of said traveling wave grid.

10. The portable apparatus according to claim 9, wherein said two traveling wave grids are oppositely charged and wherein both of said oppositely-charged circular traveling wave grids are configured in an arrangement to cause the bioagents to migrate to extraction ports located at the center of each said traveling wave grid.

11. The portable apparatus according to claim 1, comprising at least three traveling wave grids, wherein first and second traveling wave grids are patterned on the inside surface of the curved walls of a cylinder and a third traveling wave grid is patterned on the side wall of a collection slot extending the length of the curved walls of the cylinder and orthogonal to said first and second traveling wave grids, wherein said first and second traveling wave grids cause bioagents to migrate to said collection slot within said container and said third traveling wave grid causes said bioagents to migrate along said collection slot to at least one extraction port.

12. The portable apparatus according to claim 11, further comprising a center electrode for providing a bias voltage to the bioagents within said sample solution.

13. The portable apparatus according to claim 1, further comprising a high viscosity medium applied to the flow surface of said second traveling wave grid.

14. The portable apparatus according to claim 13, wherein said high viscosity medium comprises at least one member selected from the group consisting of gels and micro-pore filters.

15. The portable apparatus according to claim 1, further comprising a means for removal of collected bioagents from said at least one extraction port wherein said removal means comprises at least one member selected from the group consisting of syringe aspiration, heat melting with aspiration, and electroblotting.

16. The portable apparatus according to claim 1, wherein said bioagent particles have mobilities and wherein the apparatus has a means for generating a pulse sequence or frequency are customized to collect only particles with mobilities above a specified value.

17. The portable apparatus according to claim 1, wherein said voltage controller has a means for providing said multiphase electrical signal to said collection of buses either simultaneously or sequentially.

18. A portable apparatus for extracting and concentrating bioagents within a fluid medium, the apparatus comprising:

a container having at least one sample solution inlet port, and wherein said container comprises a parallelepiped;

traveling wave grids patterned on surfaces of said container, wherein at least one of said traveling wave grids is configured to migrate bioagents to at least one specified surface within said container to at least one extraction port, said traveling wave grids comprising:

a substrate;

a collection of closely spaced and parallel electrically conductive electrodes extending across said substrate;

a collection of buses providing electrical communication with said collection of conductive electrodes;

wherein said traveling wave grids comprise at least three traveling wave grids patterned on three surfaces of said container, including a first traveling wave grid and a second traveling wave grid patterned on opposing surfaces of said container and a third traveling wave grid patterned on a surface adjacent to both said first traveling wave grid and said second traveling wave grid; and at least one voltage controller for providing a multiphase electrical signal to said collection of buses and said collection of electrodes of said traveling wave grids and providing a four phase voltage waveform having a ninety decree separation between said phases for driving said collection of electrodes.

19. A portable apparatus for extracting and concentrating bioagents within a fluid medium, the apparatus comprising:

a container having at least one sample solution inlet port;

at least two traveling wave grids patterned on at least two surfaces of said container, wherein at least one traveling wave grid is configured so bioagents migrate to at least one specified surface within said container to at least one extraction port, said at least two traveling wave grids comprising:

a substrate;

a collection of closely spaced and parallel electrically conductive electrodes extending across said substrate;

a collection of buses providing electrical communication with said collection of conductive electrodes; and at least one voltage controller for providing a multiphase electrical signal to said collection of buses and said collection of electrodes of said at least two traveling wave grids;

a controller connection, for connecting to a controller; and a battery connection for connecting to a portable battery, wherein the controller and portable battery allow the portable device to be hand portable.

* * * * *